(12) United States Patent
Wieringa et al.

(10) Patent No.: US 11,992,597 B2
(45) Date of Patent: May 28, 2024

(54) METHOD AND MAINTENANCE DEVICE FOR AUTOMATIC MAINTENANCE OF AN AUTONOMOUS DIALYSIS SYSTEM

(71) Applicants: IMEC VZW, Leuven (BE); Stichting IMEC Nederland, Eindhoven (NL)

(72) Inventors: Fokko Wieringa, Elst (NL); Willem Van Roy, Bierbeek (BE); Patrick van Deursen, Bussum (NL); Lucas Lindeboom, Beek en Donk (NL)

(73) Assignees: Imec vzw, Leuven (BE); Stichting IMEC Nederland, Eindhoven (NL)

( * ) Notice: Subject to any disclaimer, the term of this patent is extended or adjusted under 35 U.S.C. 154(b) by 36 days.

(21) Appl. No.: 17/728,637

(22) Filed: Apr. 25, 2022

(65) Prior Publication Data
US 2022/0355013 A1 Nov. 10, 2022

(30) Foreign Application Priority Data

May 7, 2021 (EP) .................................. 21172696

(51) Int. Cl.
*A61M 1/36* (2006.01)
(52) U.S. Cl.
CPC ....... *A61M 1/3672* (2013.01); *A61M 2205/70* (2013.01)
(58) Field of Classification Search
None
See application file for complete search history.

(56) References Cited

U.S. PATENT DOCUMENTS

| | | |
|---|---|---|
| 5,431,811 A | 7/1995 | Tusini et al. |
| 5,989,438 A | 11/1999 | Fumiyama |
| 2005/0203493 A1 | 9/2005 | Kuroda et al. |

(Continued)

FOREIGN PATENT DOCUMENTS

| | | |
|---|---|---|
| WO | 2016164643 A1 | 10/2016 |
| WO | 2018237036 A1 | 12/2018 |

OTHER PUBLICATIONS

Extended European Search Report and Written Opinion, Application No. EP21172696.3, dated Oct. 28, 2021, 8 pages.

(Continued)

*Primary Examiner* — Krishnan S Menon
(74) *Attorney, Agent, or Firm* — McDonnell Boehnen Hulbert & Berghoff LLP (57) ABSTRACT

According to an aspect there is provided a method for automatic maintenance of a dialysis system. The dialysis system includes a plurality of filter sections where each filter section includes a blood flow channel, a dialysate flow channel, and a membrane separating the blood flow channel from the dialysate flow channel and having a plurality of pores through which substances are exchanged between a blood flow in the blood flow channel and a dialysate flow in the dialysate flow channel. The method includes determining, for each filter section of the plurality of filter sections, whether a maintenance criterion is fulfilled. The method also includes triggering a maintenance event for a filter section of the plurality of filter sections for which the maintenance criterion is fulfilled. The method also includes executing the maintenance event and optionally administering a thrombolytic agent to the blood flow channel of the filter section.

10 Claims, 5 Drawing Sheets

(56) References Cited

U.S. PATENT DOCUMENTS

2006/0241543 A1    10/2006  Gura
2012/0273415 A1*  11/2012  Gerber .................. A61M 1/361
                                                                210/741
2013/0274642 A1*  10/2013  Soykan ................ A61B 5/6866
                                                                604/5.01
2018/0353672 A1    12/2018  Ahmadi
2019/0134568 A1     5/2019  Roy

OTHER PUBLICATIONS

Inoue, Nagisa, and Hiroaki Onoe. "Graphene-based wireless inline pressure sensor for in vivo blood pressure monitoring." In 2019 IEEE 32nd International Conference on Micro Electro Mechanical Systems (MEMS), pp. 720-722. IEEE, 2019.

Ostadfar, Ali, Andrew H. Rawicz, and Mojgan Gitimoghaddam. "Application of backwashing to increase permeate flux in bioparticle separation." Journal of Medical and Biological Engineering 33, No. 5 (2013): 478-485.

* cited by examiner

Fig. 5

METHOD AND MAINTENANCE DEVICE FOR AUTOMATIC MAINTENANCE OF AN AUTONOMOUS DIALYSIS SYSTEM

CROSS-REFERENCE TO RELATED APPLICATIONS

The present application is a non-provisional patent application claiming priority to European Patent Application No. 21172696.3, filed May 7, 2021, the contents of which are hereby incorporated by reference.

FIELD OF THE DISCLOSURE

The present disclosure relates to maintenance of a dialysis system, and more specifically to a method and a maintenance device for automatic maintenance of an autonomous dialysis system.

BACKGROUND

Patients suffering from renal failure without immediate access to a kidney transplant are dependent on dialysis to provide filtering of toxins from the blood flow. The function of the kidneys needs to be artificially provided regularly in order to avoid poisoning and death of the patients.

Thus, patients may require dialysis procedures frequently. The dialysis procedure is time consuming and highly affects life of the patients and is also associated with high costs for society. In this respect, it is important that dialysis is efficient in order to improve health of the patients. Two main types of dialysis exist: peritoneal dialysis and hemodialysis. This disclosure focuses on hemodialysis.

A hemodialysis device typically includes a dialysis filter (dialyzer) which is composed of a large number of parallel filter sections (mostly in the form of hollow fibers), each of which comprises a membrane through which fluid exchange between a blood flow channel and a dialysate flow channel is provided. The function of the membrane is to allow toxins to pass through pores of the membrane so as to remove toxins from the blood flow into the dialysate flow. The membrane allows filtering of toxins through the membrane based on the size of the pores.

A significant challenge of artificial kidneys, as well as with all other stationary, wearable or implantable devices comprising a blood circuit, is the effect of blood clotting. Over time, blood clots are likely to form on the blood flow side of the membrane, which eventually leads to clogging of the pores and potentially also of the entire blood flow channel used for dialysis. Blood clotting decreases the efficiency of the dialysis through the membrane, jeopardizing the health of the patient. In the present art, clotting beyond a certain percentage of the dialyzer fibers requires replacement of the dialyzer by medical personnel. Consequently, the patient is required to visit a hospital, where trained personnel can act if needed, or the patient can be trained to exchange a dialyzer at home. For wearable devices, intended to function during daily life, it would be highly advantageous that the filter is kept clean automatically, without the need for a manual exchange (with risks on hygiene and blood loss). For implantable devices, replacement and cleaning/repair even means a need for surgery, which makes this priority even higher.

As a main defense against blood clotting within (still experimental) implantable dialyzers, today's solutions utilize careful flow-dynamic design and an anti-clotting surface coating considerably slowing down the process of blood clotting. The duration until blood clotting, and thus requirement of replacement or cleaning/repair, of artificial kidneys may thus lie in the order of several weeks to a month.

However, for medical viability, and especially for implantable devices, the device should be able to function for 2 years at the very least, and preferably up to 5 years, without the need of any surgical repair/replacement. Hence, there is a need in the art for further improvements related to the life cycle of artificial devices with blood circuits, such as implantable artificial kidneys.

SUMMARY

An objective of the present disclosure is to mitigate, alleviate or eliminate one or more of the above-identified deficiencies in the art and disadvantages singly or in any combination. These and other objects are at least partly met by the disclosure as defined in the independent claims. Various other example embodiments are set out in the dependent claims.

According to a first aspect of the present disclosure there is provided a method for automatic maintenance of a dialysis system, wherein the dialysis system comprises a plurality of filter sections, wherein each filter section of the plurality of filter sections comprises a blood flow channel, a dialysate flow channel, and a membrane separating the blood flow channel from the dialysate flow channel and having a plurality of pores through which substances are exchanged between a blood flow in the blood flow channel and a dialysate flow in the dialysate flow channel, the method comprising:

determining, for each individual filter section of the plurality of filter sections, whether a maintenance criterion is fulfilled;

triggering a maintenance event for a filter section of the plurality of filter sections for which the maintenance criterion is fulfilled;

executing the maintenance event for the filter section, wherein said executing comprises:

administering a thrombolytic agent to the blood flow channel of the filter section.

By the term "dialysis system" is here meant any unit, device or element comprising a blood circuit with a membrane allowing toxins to pass through pores of the membrane so as to remove toxins from the blood flow. The dialysis system may be arranged in relation to the patient in a number of different manners. By way of example, the dialysis system may be a dialysis system which is implantable into a patient, or it may be a dialysis system that is externally wearable by a patient such that the filter is external to the body of the patient. The afore-mentioned systems are systems that the patient always carries and is continuously removing toxins from the blood flow. By way of further example, the dialysis system may be a stationary dialysis system such as a stationary dialysis system at a hospital. In the latter case the dialysis system is not continuously carried by the patient, but instead the patient is required to periodically visit a hospital for regular consultation and treatment. The following description will henceforth focus on implantable dialysis systems or wearable dialysis systems carried by the patient, however it should be noted that the method for automatic maintenance is applicable also to a stationary dialysis system.

By the term "maintenance criterion" is here meant a criterion of whether a blood flow channel is in need of maintenance. By way of example, maintenance of a blood flow channel may be preventive maintenance, thus maintenance needed as a measure for preventing blood clotting and thereby maintain the full filtering efficiency of the filter section. By way of further example, maintenance of a blood flow channel may also be corrective maintenance, thus maintenance needed as a measure for cleaning if blood clotting has occurred, in order to dissolve or remove clots and thereby repair the dialysis system to restore the filtering efficiency of the filter section in question. Henceforth, the terms "corrective maintenance" and "repair" are used interchangeably in the present disclosure.

By the term "thrombolytic agent" is here meant any liquid compound or solution with the property of dissolving blood clots or the onset thereof, for medical purposes, without harming the materials out of which the dialysis system is made. By way of example, the thrombolytic agent may comprise, but is not limited to, Streptokinase, Alteplase, Reteplase, Tenecteplase, Urokinase, Prourokinase, and/or Anistreplase (APSAC).

It is conceivable that a single thrombolytic agent is used, and thus the same type of thrombolytic agent is used for preventive and corrective maintenance. It is equally conceivable that more than one, for example two, thrombolytic agents are used. By way of example, a mild thrombolytic agent may be used for preventive maintenance, whereas a strong thrombolytic agent may be used for corrective maintenance. By way of further example, a mild thrombolytic agent may be a thrombolytic agent that is not harmful to the body and may therefore not require a waste reservoir, whereas a strong thrombolytic agent may be harmful to the body and may therefore need to be discarded to a waste reservoir after being used for maintenance.

By way of example, administering a thrombolytic agent to the blood flow channel may be achieved by providing a flow of the thrombolytic agent through the blood flow channel of the filter section, or through the dialysate flow channel of the filter section and then via the filter pores reaching the blood flow channel, for which a maintenance criterion is fulfilled. Given as a non-limiting example, administering the thrombolytic agent may involve switching, at a blood flow channel inlet, from a blood inlet at which blood from the patient is supplied to the filer section, to a thrombolytic agent inlet through which a flow of thrombolytic agent is supplied to the filter section. Given as another non-limiting example, administering the thrombolytic agent may involve switching, at a dialysate flow channel inlet, from a dialysate inlet at which dialysate is supplied to the filter section, to a thrombolytic agent inlet through which a flow of thrombolytic agent is supplied to the filter section.

The method for automatic maintenance of a dialysis system may be implemented into a maintenance device such that the maintenance device performs the method. It should be understood that there may be other steps in achieving dialysis which are not part of the method for automatic maintenance performed by the maintenance device. For example, in case the dialysis system forms an implanted artificial kidney, there may be steps related to how the dialysis system, and thus also the maintenance device, is put in place and connected to the patient. These steps are not performed by the maintenance device but may rather be performed e.g. by a surgeon. Hence, such steps are not part of the method performed by the maintenance device. Further, there may be steps related to how thrombolytic agent is filled or re-filled for allowing control of administering of thrombolytic agent by the maintenance device. Also, there may be steps related to how waste fluid may be drained after a thrombolytic agent has been administered. Such steps are also not performed by the maintenance device itself but may rather be performed by medical personnel or a trained patient. Hence, such steps are also not part of the method for automatic maintenance as performed by the maintenance device.

The method for automatic maintenance may be performed by a processing unit which may receive input information from sensors, and which may provide control signals for controlling actions, such as administering of the thrombolytic agent.

The processing unit may be implemented as a general-purpose processing unit, such as a central processing unit (CPU), which may execute the instructions of one or more computer programs in order to implement the method. The processing unit may alternatively be implemented as firmware arranged in an embedded system, or as a specifically designed processing unit, such as an Application-Specific Integrated Circuit (ASIC) or a Field-Programmable Gate Array (FPGA), which may be configured to implement the method.

The maintenance device may be configured to execute a predetermined number of maintenance events such that the dialysis system is regularly cleaned, thereby keeping the dialysis system in good working order for a longer time than what would otherwise be possible by using a conventional dialysis system without an active maintenance device for automatic maintenance. In this manner, the time between two consecutive hospital visits at which the device requires replacement of parts or cleaning/repair of the clogged channels by medical personnel, may be significantly increased, prolonging the durability of any given anti-fouling coating.

The number of applicable maintenance events may be determined by a number of different factors. Given as non-limiting examples, factors that may determine the number of applicable maintenance events may be battery life of the maintenance device performing the maintenance, degradation of surfaces in the blood flow channel to be cleaned, available volume of thrombolytic agent, and the size of a possible waste reservoir. It should be noted that technologies for wireless recharging to the battery are presently available, and if such technologies are applied, the battery life may not be a limiting factor.

It should be understood that, although the description henceforth is focused on a dialysis system, such as an artificial kidney, the method for automatic maintenance may be equally applicable to other systems comprising a blood circuit, such as artificial pancreas, artificial livers, etc.

An advantage with the present disclosure is that the lifetime of the dialysis system during which no attention of medical personnel is required may be significantly prolonged. This may provide medical benefits for the patient, as longer intervals between hospital visits may be achieved. This is a significant advantage not least to patients with implanted dialysis systems, since it may allow long intervals between surgeries and freedom to move around. Further, it may also lead to financial benefits, as long intervals between hospital visits may reduce labor time for medical personnel. It may also reduce the need for consumables and/or replacement parts of the dialysis system, since the filter sections are regularly cleaned whereby the filter sections are maintained functional for much longer than what would otherwise be possible with a conventional dialysis system.

Another advantage with the present disclosure is that it allows for surgical interventions being much better plannable. For example, since the time interval between necessary hospital visits may be prolonged from a few weeks to a couple of years, visits may be planned well in advance of the next hospital visit. Further, the method may allow for messages to be sent to the patient and/or the doctor responsible for the treatment, informing about maintenance events and/or a condition of the dialysis system. By way of example, the messages may be sent to an application of a mobile device such as a mobile phone or a tablet. The information from such messages may be used for e.g. adjusting the time plan for the next hospital visit. Further, information about failure of specific filter sections and the number of spare sections left may be provided, allowing for planning of an additional hospital visit for repair or replacement of the filter section, in advance of health of the patient beginning to be noticeably affected.

Yet another advantage of the present disclosure is that it allows for combination with already existing devices using membrane-based approaches for dialysis. In other words, the method for automatic maintenance may be implemented for already existing dialysis systems, and thus no development of a new dialysis membrane system is required.

Also, the present disclosure may be combined with anti-clotting surface coatings slowing down the process of blood clotting. Thus, the anti-clotting surface coatings may function to prolong a time between maintenance events performed by the method, whereas administration of the thrombolytic agent may ensure that any impaired functionality due to blood clotting occurring despite the anti-clotting surface coatings may be restored.

According to an embodiment, the determining whether a maintenance criterion is fulfilled comprises:
  determining whether a preventive maintenance criterion is fulfilled comprising determining whether a time duration since a nearest preceding maintenance event for the filter section is above a predetermined threshold.

The predetermined threshold may be set to a time duration during which only mild fouling of the wall is expected to occur during normal operation conditions of the dialysis system. In case no severe flow obstruction or even blockage by clotting has occurred, the maintenance event is likely to be successful. By the present arrangement, a method with which maintenance of the blood flow channels are regularly and periodically performed may be provided.

An advantage with this embodiment is that, by only mild fouling the efficiency of the filter section is likely not significantly reduced, and therefore the fouling may not yet have affected the health of the patient. By regularly cleaning the blood flow channels of the filter section when only mild fouling has occurred may provide a membrane with a more uniform efficiency of filtering toxins from the blood, over longer time periods.

Another advantage of this embodiment is that, since cleaning of the blood flow channel is likely to be more successful if only mild fouling has occurred as compared to when severe flow restriction or clotting has occurred, the method may provide a longer total operational time for the individual blood flow channels in the filter sections, and thereby may prolong the lifetime of the dialysis system.

According to an embodiment, the determining whether a maintenance criterion is fulfilled comprises:
  determining whether a corrective maintenance criterion is fulfilled comprising measuring, by at least one sensor per filter section, at least one parameter of the blood flow flowing through the blood flow channel of the filter section, prior to entry into the blood flow channel, inside the blood flow channel, and/or after exiting the blood flow channel;
  wherein the at least one parameter being any one from a blood flow rate, a blood flow pressure, a blood flow chemistry, a blood flow ion content, an electrical conductivity, an ultrasonic transmission or reflection parameter, and a presence of blood clots.

Given as a non-limiting example the measuring may be performed by a sensor arranged at a blood inlet or a blood outlet of the maintenance device, or a combination thereof. By the present arrangement, incoming arterial blood pressure and flow rate may be measured. Further, blood flow chemistry and ion content such as the concentration of Na+, K+, Ca2+, Cl− and pH may be measured.

Given as another non-limiting example, the measuring may be performed by a sensor arranged at a blood flow channel inlet or a blood flow channel outlet of individual filter sections of the maintenance device, or a combination thereof. By the present arrangement, pressure and flow rate per filter section may be measured so as to identify deterioration of blood flow through the filter section which may identify nearly clogged filter sections.

Given as yet another non-limiting example, the measuring may be performed by a sensor arranged on the membranes of the blood flow channels of individual filter sections. By the present arrangement, pressure and flow rate along the individual membranes may be measured. Such measurements may enable detection of the onset of clogging of individual membranes.

Given as yet another non-limiting example, the measuring may be performed by an ultrasonic sensor arranged on in the blood flow channels of individual filter sections. According to one embodiment, an ultrasonic transducer may be arranged by the blood flow channel inlet and another ultrasonic transducer may be plated by the blood flow channel outlet, of each of the individual blood flow channels. The two ultrasonic transducers may be connected to a counter-phase generator such that the ultrasonic transducers emit ultrasonic waves that are in counterphase with each other. If no blood clotting has occurred in the blood flow channel, the ultrasonic waves are not obstructed and may thus extinguish each other by destructive interference between the ultrasonic waves, measured by a third ultrasonic transducer in the middle. However, if blood clotting has occurred, the blood clots may cause anisotropy in the blood flow channel and the two ultrasonic waves may be obstructed by the blood clots in the blood flow channel, and consequently full extinction of the ultrasonic waves will not occur. Upon interference between the two ultrasonic waves, there may thus be a remaining ultrasonic wave. The remaining ultrasonic wave resulting from anisotropy in the blood flow channel may be detected by an ultrasonic sensor arranged centrally in the blood flow channel between the blood flow channel inlet and outlet, and thus in between the two ultrasonic transducers. By the present arrangement, the presence and location of blood clots may be measured.

It is conceivable that the maintenance device may comprise a single type of sensor measuring a single type parameter. However, it is equally conceivable that the maintenance device may comprise a plurality of different types of sensors measuring a plurality of different parameters.

An advantage with this embodiment is that a maintenance event, in this case a maintenance event for corrective maintenance, may be triggered and executed upon detection of presence of blood clots in the blood flow channel, and the blood flow channel may thereby be cleaned from blood clots at an early stage of clotting.

Another advantage with the present embodiment is that, even if combined with periodic maintenance executed when the time duration since a nearest preceding maintenance event exceeds the predetermined threshold, clots may be detected at an early stage even in between periodic maintenance events and the blood flow channel may be cleaned before the next periodic maintenance event takes place. The device may further be equipped with a "learning" function that can shorten the time between preventive maintenance cycles per filter section.

It should be understood that the determining whether a corrective maintenance criterion is fulfilled may further comprise determining whether a time duration since a nearest preceding maintenance event for the filter section is above a predetermined threshold. It should be understood that determining whether a preventive maintenance criterion is fulfilled may further comprise measuring, by at least one sensor per filter section, a parameter of the blood flow flowing through the blood flow channel of the filter section, prior to entry into the blood flow channel, inside the blood flow channel, and/or after exiting the blood flow channel.

According to an embodiment, the executing the maintenance event for the filter section further comprises:
switching, at a blood flow channel inlet, from a blood inlet to a thrombolytic agent inlet.

Switching may be made by any type of inlet switches for switching between different liquid flows. By way of example, the switching may be accomplished by, but is not limited to, any type of valve for liquid applications.

By way of example, a switch may comprise a single inlet and a single outlet, wherein the switch may switch between connecting and disconnecting the inlet to the outlet, thereby either allowing a liquid to flow through the switch or preventing a liquid flow to flow through the switch.

By way of example, a switch may comprise two inlets and a single outlet, wherein the switch may switch between connecting the first inlet to the outlet, and connecting the second inlet to the outlet, thereby allowing liquid from only one inlet at a time to flow through the switch. The present arrangement may also allow disconnecting both the first and the second inlets from the outlet, thereby preventing liquid at both inlets to flow through the switch.

By way of example, a switch may comprise two outlets and a single inlet, wherein the switch may switch between connecting the first outlet to the inlet, and connecting the second outlet to the inlet, thereby allowing liquid from the inlet to flow through the switch to only one outlet at a time. The present arrangement may also allow disconnecting both the first and the second outlets from the inlet, thereby preventing liquid to flow through the switch.

An advantage with this embodiment is that the thrombolytic agent may act without more blood also entering the blood flow channel that would dilute the thrombolytic agent or contribute to further extension of the blood clot. In this manner, the thrombolytic agent in the blood flow channel may remain at a high local concentration and thereby the dissolving of blood clots may be accomplished more efficiently and thus during a shorter period of time. In other words, the maintenance event may be short, and the blood flow channel may be quickly reconnected to the blood flow again for further filtering of blood by the dialysis system.

However, it should be realized that the flow through the filter section need not necessarily be completely switched from blood flow to thrombolytic agent flow. Rather, the thrombolytic agent may also be mixed with a lowered flow rate of blood through the blood flow channel. In this sense the device might be equipped with "mild" thrombolytic agents of which small amounts can be tolerated entering into the main blood circulation, versus more "aggressive" thrombolytic agents, that need to be disposed of in a waste reservoir.

According to an embodiment, the executing the maintenance event for the filter section further comprises:
switching, at a dialysate flow channel inlet, from a dialysate inlet to a thrombolytic agent inlet.

According to an embodiment, the method further comprises:
opening a blood flow channel inlet in a spare filter section, such that the number of filter sections operating with blood flow is constant, thereby maintaining full capacity of the dialysis system.

With a dialysis system having a number of spare filter sections, redundancy is created for maintenance.

By way of example, said spare filter sections may initially be disconnected from the blood flow being unused until needed. When a filter section in need of maintenance is to be isolated from the blood flow by means of inlet switches, and temporarily connected to a thrombolytic agent inlet for cleaning, one of the spare filter sections may be connected to the blood flow, taking the disconnected filter sections place in order to maintain a constant number of operational filter sections. After rinsing, the cleaned filter section may be re-connected to the blood flow, or alternatively be kept aside as a spare section. Upon re-connecting the cleaned filter section, the original spare filter section may be re-disconnected from the blood flow. The re-disconnected spare filter section may be stored filled with mild thrombolytic agent.

Filter sections may reach a point at which the filtering efficiency may no longer be restored despite repeated maintenance events. In such a case, the filter section may be classified as irreparable, and thereby need to be permanently disconnected from the blood flow. By way of example, when a filter section may need to be permanently disconnected from the blood flow, a spare filter section may be connected to the blood flow, thereby taking the disconnected filter sections place permanently, such that the number of functional filter sections remains constant.

By way of further example, a dialysis system with a redundancy of filter sections may initially have all the available filter sections connected to the blood flow, thereby running on an over-capacity of filter sections. Upon filter sections eventually being used beyond maintenance, individual filter sections may be disconnected from the blood flow, until the remaining number of connected filter sections has reached a level of what is required for full filtering capacity.

Information about the number of available filter sections, the number of unused spare filter sections, and/or the number of irreparable filter sections may be logged into e.g. a memory of a processing unit in the maintenance device. The information may be communicated to the user interface to inform the patient and/or a medical supervisor about the current status of the maintenance device.

An advantage with this embodiment is that, even as some filter sections reach a point beyond maintenance and therefore need to be disconnected from the blood flow, the full filtering capacity of the dialysis system may still be maintained and that replacement surgery may be planned ahead (elective surgery is preferable above emergency surgery).

According to an embodiment, the executing the maintenance event for the filter section further comprises:
switching, at a blood flow channel outlet, from a blood outlet to a thrombolytic agent outlet.

By switching at the blood flow channel outlet, by means of an outlet switch, from a blood outlet leading to returning the filtered blood to ordinary blood flow of the patient, to a thrombolytic agent waste outlet, it may be ensured that the thrombolytic agent and/or dangerous debris does not reach into the blood flow of the body of the patient.

An advantage with this embodiment is that also thrombolytic agents which may be harmful to a human body may be acceptable as an agent for cleaning the blood flow channels of the dialysis system. Hence, more aggressive thrombolytic agents which may be very efficient in dissolving blood clots and cleaning the blood flow channels may be used.

According to an embodiment, the executing the maintenance event for the filter section further comprises:
receiving, at the inlet of the blood flow channel, the thrombolytic agent from a supply reservoir configured to store the thrombolytic agent.

A supply reservoir may be arranged as a part of, or connected to, the maintenance device. The supply reservoir may be configured to store a predefined amount of thrombolytic agent, or thrombolytic agent for a predetermined number of maintenance events.

An advantage with this embodiment is that the maintenance device may have thrombolytic agent available for a number of maintenance events that may last for 1 year, preferably 2 years, and more preferably S years.

It should be realized that the supply reservoir may be re-filled at a visit to a hospital or a health center or by a trained patient. Thus, in order to avoid regular visits, the supply reservoir may store thrombolytic agent that lasts for a long period of time. However, if the supply reservoir is to store thrombolytic agent that lasts for a long period of time, a volume of the supply reservoir needs to be relatively large. It may be desired that the supply reservoir is small as the supply reservoir may be implanted into a patient, since a small volume of the supply reservoir limits an impact of the supply reservoir being implanted. Hence, the volume of the supply reservoir may be chosen in view of the impact on implanting the supply reservoir and a required time between visits to a hospital or a health center.

According to an embodiment, the executing the maintenance event for the filter section further comprises:
discarding, at the outlet of the blood flow channel, the thrombolytic agent to a waste reservoir configured to store waste thrombolytic agent.

A waste reservoir may be arranged as a part of, or connected to, the maintenance device. The waste reservoir may be configured to store a predefined amount of waste thrombolytic agent, or waste thrombolytic agent from a predetermined number of maintenance events. In addition to storing waste thrombolytic agent, the waste reservoir may also be configured to store any chemical waste that is incompatible with the bladder, such as disposed blood clot fragments, and rinsing fluid in cases when a rinsing fluid is used to rinse out the thrombolytic agent from the blood flow channel prior to re-connecting the blood flow channel to the blood flow of the patient.

It should be understood that waste thrombolytic agent may comprise thrombolytic agent that has been used for maintenance of a blood flow channel. Depending on whether blood clotting had occurred in the blood flow channel prior to maintenance, the blood clot debris may be discarded to the waste reservoir together with the waste thrombolytic agent.

An advantage with this embodiment is that the maintenance device may use thrombolytic agents that may be incompatible with or even harmful to the human body, e.g. the bladder, without letting the waste thrombolytic agent out into the body of the patient.

It should be understood that the supply reservoir for thrombolytic agent as well as a waste reservoir for waste thrombolytic agent may be applied for any type of dialysis system. However, for use with implantable dialysis systems, the reservoirs may be of high importance, yet the volumes of reservoirs for thrombolytic agent and waste fluid are limited. However, even for implantable systems it is conceivable that the reservoirs may be made accessible from the outside with a transdermal needle, by the reservoirs being implanted close to the skin. Such types of transdermally refillable reservoirs are also known in the present art.

Filling and/or draining of drug and waste reservoirs can be done at a convenient moment. However, it should be pointed out that such steps are performed by medical personnel, whereas the maintenance device is configured to autonomously control flow between the reservoirs and the dialysis system. Hence, steps of filling of the supply reservoir and draining of the waste reservoir are thus not part of the method for automatic maintenance as autonomously performed by the maintenance device. Of course, signaling the need for refilling or emptying reservoirs may be part of the automatic maintenance device.

According to an embodiment, the method further comprises:
determining, upon finalizing the maintenance event for the filter section, whether the maintenance event was successful;
upon the maintenance event not being successful, repeating the maintenance event up to a maximum number of attempts;
determining, upon finalizing the maximum number attempts of maintenance events, whether the maintenance event was successful;
classifying, upon the maintenance event not being successful and after reaching the maximum number of attempts, the filter section as irreparable;
connecting, upon the filter section being classified as irreparable, a spare filter section to the blood flow.

By way of example, determining whether a maintenance event was successful may be performed for a preventive maintenance event or a corrective maintenance event.

By way of example, determining whether the maintenance event was successful may be made by using any available sensor in the system, to check whether there may still be blood clots present in the blood flow channel.

In case it is determined that the maintenance event was not successful, the presence of at least some blood clots may be detected, further maintenance may be required. The maintenance event may be repeated followed by a new determining whether the maintenance event was successful. This may be repeated up to a maximum number of attempts to clean and/or repair the blood flow channel. The maximum number of attempts for which the maintenance event may be repeated, may be predetermined. By way of example, the maximum number of attempts may be a factory default setting, or it may be set by the medical personnel responsible for the treatment of the patient, at the start of treatment. Further, the maximum number of attempts may be a programmable value. By way of example, a programmable value may be changed by medical personnel and/or the patient. By way of further example, a programmable value may be altered automatically by the maintenance device for example based on data from previous maintenance events from which it may be determined that a higher or lower maximum number of attempts for maintenance may be suitable for the patient in question.

If the maximum number of attempts for maintenance is reached and the maintenance is still determined not to be successful, the filter section may be classified as irreparable. An irreparable filter section may be permanently disconnected from the blood flow. By way of example, the filter section may be disconnected by switching at the inlet and outlet of the blood flow channel such that the inlet and outlet are closed, and thus no fluid may flow in or out of the filter section.

Upon the filter section being classified as irreparable, a spare filter section may be connected to the blood flow, permanently replacing the irreparable filter section.

An advantage with this embodiment is that maintenance is continued until the blood flow channel is clean from blood clots. In this manner, build-up of fouling over time may be avoided, even if a single maintenance event should not be sufficient for cleaning the blood flow channel.

Another advantage with this embodiment is that if the corrective maintenance event is not successful even after a maximum number of attempts, the filter section is likely permanently affected by decreased efficiency, and by opening a spare filter section the number of working filter sections may be kept constant and the dialysis system is thereby maintaining the full capacity.

According to an embodiment, the method further comprises:
  sending a wireless message to an external unit, the wireless message including information about a status of the plurality of filter sections of the dialysis system.

By the term "external unit" is here meant a unit that is external to the maintenance device. By way of example, an external unit may be a computer, a mobile phone or a tablet. An external unit may be the property of a hospital or medical personnel. An external unit may also be the property of the patient.

It is conceivable that the wireless message is sent directly to the external unit. It is equally conceivable that the wireless message is sent to the external unit via one or more intermediate devices. By way of example, an intermediate device may be a network router.

By way of example, information such as a filter section being classified as being irreparable and/or a spare filter section is being connected to the blood flow and/or the number of remaining spare filter sections available in the system, may be wirelessly sent to an external unit. The information may prompt the patient to contact medical personnel at a hospital, or schedule an appointment at the hospital. The information may assist medical personnel to for example reschedule or plan an upcoming hospital visit or surgery.

An advantage with this embodiment is that status of the dialysis system may be reported allowing planning of visits to the hospital. Thus, visits may be planned well in advance of health of the patient beginning to be noticeably affected.

According to an embodiment, the executing the maintenance event for the filter section further comprises:
  emitting, by one or more ultrasonic transducers, an ultrasonic signal into the blood flow channel, whereby the declotting effect of the applied thrombolytic agent is amplified.

An ultrasonic transducer may be arranged in connection with each of the blood flow channels. By way of example, the ultrasonic transducer may be in the form of a miniature ultrasonic element. In some embodiments, the ultrasonic element is arranged on, but is not limited to, an outer wall of the blood flow channel of the individual filter sections. By emitting, by the ultrasonic transducer, an ultrasonic signal through the blood flow channel the onset of blood clotting may be prevented. Further, in case clogging of the blood flow channel has occurred, the ultrasonic signal may increase the declogging efficiency of the thrombolytic agent, during the maintenance event. By way of example, the declotting effect of the applied thrombolytic agent may be amplified by mechanical agitation as a result of the emitted ultrasonic signal.

An advantage with this embodiment is that, since the ultrasonic signal increases the declogging efficiency of the thrombolytic agent, less thrombolytic agent may be used in each maintenance event as compared to a maintenance event without any emitting of an ultrasonic signal. Consequently, the available thrombolytic agent may be sufficient for a higher number of maintenance events or be able to dissolve bigger clots than if ultrasonic signal is not used, which may further prolong the operation and the lifetime of the dialysis system.

According to a second aspect of the present disclosure there is provided a maintenance device for automatic maintenance of a dialysis system, wherein the dialysis system comprises a plurality of filter sections, wherein each filter section of the plurality of filter sections comprises a blood flow channel, a dialysate flow channel, and a membrane separating the blood flow channel from the dialysate flow channel and having a plurality of pores through which substances are exchanged between a blood flow in the blood flow channel and a dialysate flow in the dialysate flow channel, the maintenance device comprising:
  a processing unit configured for:
    determining, for each filter section of the plurality of filter sections, whether a maintenance criterion is fulfilled;
    triggering a maintenance event for a filter section of the plurality of filter sections for which the maintenance criterion is fulfilled;
    executing the maintenance event for the filter section, wherein said executing comprises:
    sending a control signal to an inlet switch for administering a thrombolytic agent to the blood flow channel of the filter section.

By way of example, the inlet switch may be connected to a blood flow channel inlet of the filter section. The inlet switch may be further configured to, as a response to receiving the control signal, switch from connecting the blood flow channel inlet to the blood inlet and connecting the blood flow channel inlet to the thrombolytic agent inlet, thereby allowing administering a thrombolytic agent through the blood flow channel of the filter section.

By way of further example, the inlet switch may be connected to a dialysate flow channel inlet of the filter section. As a response to receiving the control signal, the inlet switch may switch from connecting the dialysate flow channel inlet to a dialysate inlet and connecting the dialysate flow channel inlet to the thrombolytic agent inlet, thereby allowing administering a thrombolytic agent to the blood flow channel of the filter section via the dialysate flow channel and the membrane.

According to an embodiment, the maintenance device further comprises:
  a thrombolytic agent inlet configured to receive a thrombolytic agent feed into the maintenance device.

According to an embodiment, the maintenance device further comprises a blood inlet configured to receive a blood flow feed into the maintenance device.

According to an embodiment, the maintenance device further comprises a plurality of inlet switches, each inlet switch of the plurality of inlet switches being connectable to a filter section of the plurality of filter sections such that different inlet switches are connectable to different filter sections, wherein each inlet switch of the plurality of inlet switches is further connected to the thrombolytic agent inlet, and wherein each inlet switch of the plurality of inlet switches is configured for switching between connecting and disconnecting the thrombolytic agent inlet to the filter section.

According to an embodiment, the maintenance device further comprises:

a plurality of outlet switches, each outlet switch of the plurality of outlet switches being connected to a blood flow channel outlet of a blood flow channel in the plurality of filter sections such that different outlet switches are connected to blood flow channel outlets of different filter sections, wherein each outlet switch of the plurality of outlet switches is further connected to a thrombolytic agent outlet and connected to a blood outlet, and wherein each outlet switch of the plurality of outlet switches is configured for switching between connecting the blood flow channel outlet to the blood outlet and connecting the blood flow channel outlet to the thrombolytic agent outlet;

and wherein the executing further comprises:

sending a control signal to an outlet switch connected to a blood flow channel outlet of the filter section;

wherein each outlet switch of the plurality of outlet switches is further configured to, as a response to receiving the control signal, switch from connecting the blood flow channel outlet to the blood outlet to connecting the blood flow channel outlet to the thrombolytic agent outlet.

According to an embodiment, the maintenance device further comprises a sensor configured to measure a parameter of the blood flow flowing through the blood flow channel of the filter section, prior to entry into the blood flow channel, inside the blood flow channel, and/or after exiting the blood flow channel;

wherein the parameter being any one from a blood flow rate, a blood flow pressure, a blood flow chemistry, a blood flow ion content, and an ultrasonic signal.

According to a third aspect of the present disclosure there is provided a kit of parts for automatic maintenance of a dialysis system, the kit of parts comprises:

a maintenance device according to the second aspect;

a supply reservoir configured to store the thrombolytic agent, the supply reservoir being connectable to the maintenance device so as to supply a thrombolytic agent feed to the maintenance device; and a dosage pump configured to pump the thrombolytic agent from the supply reservoir to the blood flow channel.

The dosage pump may be configured to provide the correct dosage of the thrombolytic agent from the supply reservoir to the blood flow channel. Alternatively, the dosage pump may be connected to or embedded into the processing unit of the maintenance device, such that the processing unit may control the operation of the dosage pump. By way of example, the dosage pump may be, but is not limited to, a miniature piezo-powered dosage pumps, or a silicon chip micro-electromechanical systems (MEMS) device.

The kit of parts may be delivered as a package allowing the kit of parts to be combined into a dialysis system for providing automatic maintenance of the dialysis system.

According to an embodiment, the kit of parts further comprises a waste reservoir configured to store waste thrombolytic agent, the waste reservoir being connectable to the maintenance device so as to receive the waste thrombolytic agent and blood clot debris from the maintenance device.

According to an embodiment, the dialysis system is connectable to the maintenance device such that the blood flow channel inlet of the blood flow channel in each of the plurality of filter sections is connectable to an inlet switch of the plurality of inlet switches of the maintenance device such that blood flow channel inlets of different filter sections are connectable to different inlet switches.

According to a fourth aspect of the present disclosure there is provided a computer program product for automatic maintenance of a dialysis system, wherein the dialysis system comprises a plurality of filter sections, wherein each filter section of the plurality of filter sections comprises a blood flow channel, a dialysate flow channel, and a membrane separating the blood flow channel from the dialysate flow channel and having a plurality of pores through which substances are exchanged between a blood flow in the blood flow channel and a dialysate flow in the dialysate flow channel, wherein the computer program product comprises computer-readable instructions such that when executed by a processing unit, the computer program product will cause the processing unit to perform:

determining, for each filter section of the plurality of filter sections, whether a maintenance criterion is fulfilled;

triggering a maintenance event for a filter section of the plurality of filter sections for which the maintenance criterion is fulfilled;

executing the maintenance event for the filter section, wherein said executing comprises:

sending a control signal to an inlet switch for administering a thrombolytic agent to the blood flow channel of the filter section.

Effects and features of the second, third and fourth aspects are largely analogous to those described above in connection with the first aspect. Embodiments mentioned in relation to the first aspect are largely compatible with the second, third and fourth aspects. It is further noted that the present disclosure relates to all possible combinations of features unless explicitly stated otherwise.

Other objectives, features and advantages will be evident from the following detailed disclosure, from the attached claims as well as from the drawings.

BRIEF DESCRIPTION OF THE FIGURES

The above, as well as additional objects, features and advantages of the present disclosure, will be better understood through the following illustrative and non-limiting detailed description, with reference to the appended drawings. In the drawings like reference numerals will be used for like elements unless stated otherwise.

DETAILED DESCRIPTION

In cooperation with attached drawings, the technical contents and detailed description of the present disclosure are described thereinafter according to one or more example embodiments, being not used to limit the claimed scope. The present disclosure may be embodied in many different forms and should not be construed as limited to the embodiments set forth herein; rather, these embodiments are provided for thoroughness and completeness, and fully convey the scope of the present disclosure to the skilled person.

Figure 1:
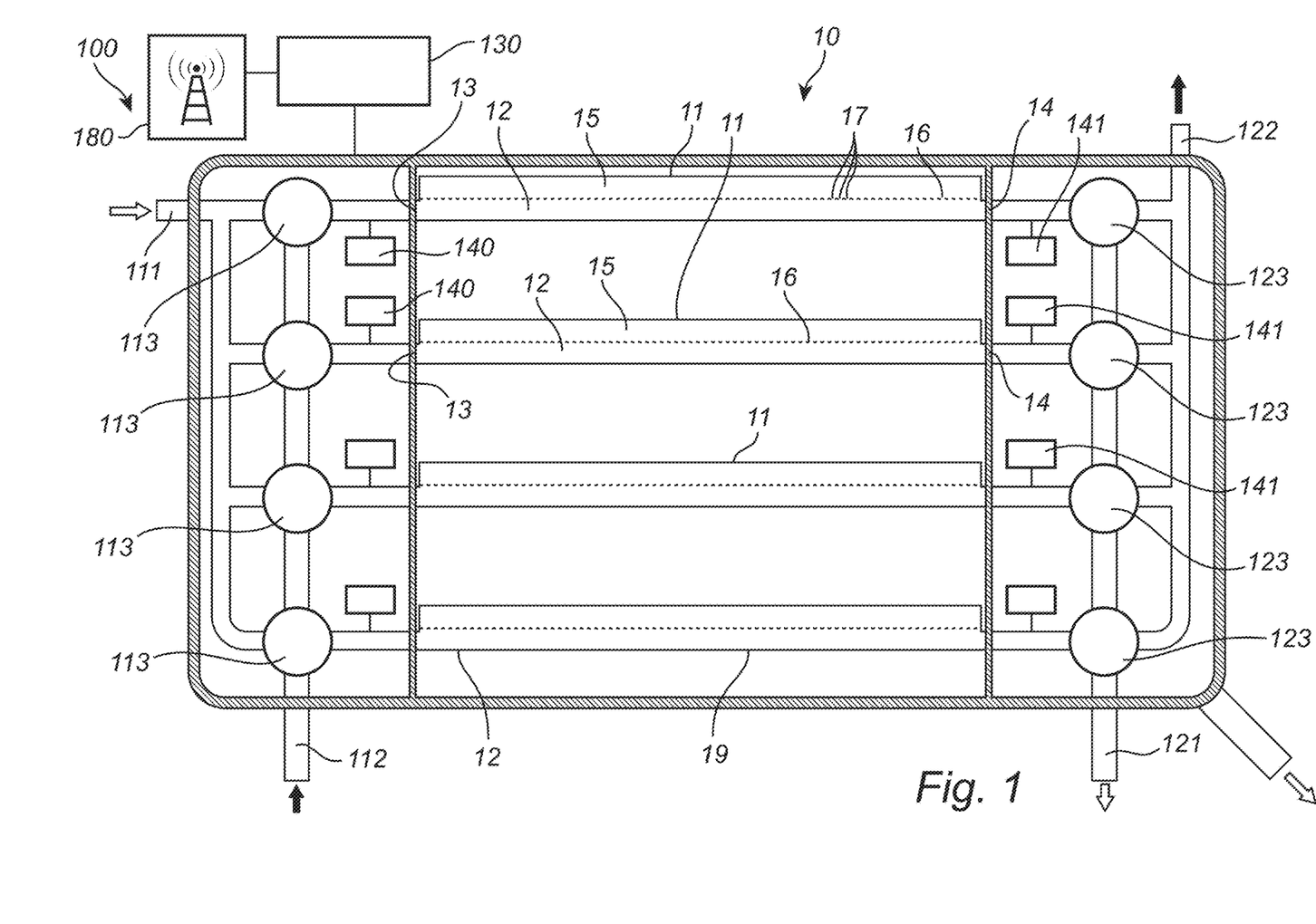
FIG. 1 illustrates a detailed view of a maintenance device for automatic maintenance of a dialysis system, according to an example embodiment.

FIG. 1 illustrates a maintenance device 100 for automatic maintenance of a dialysis system 10. The maintenance device 100 comprises a blood inlet 112 configured to receive a blood flow feed from a patient's blood stream when connected to a patient. The maintenance device 100 further comprises a plurality of inlet switches 113, each of which are connected to the blood inlet 112 such that the blood flow received at the blood inlet 112 is distributed to the plurality of inlet switches 113.

The maintenance device 100 further comprises a thrombolytic agent inlet 111 configured to receive a thrombolytic agent feed into the maintenance device 100. The thrombolytic agent inlet 111 is connected to each of the inlet switches 113 such that the received thrombolytic agent is distributed to the plurality of inlet switches 113.

The dialysis system 10 comprises a plurality of filter sections 11, each of which comprises a blood flow channel 12 with a blood flow channel inlet 13 and a blood flow channel outlet 14. Each of the inlet switches 113 is further connected to a corresponding blood flow channel 12 via the blood flow channel inlet 13.

Each inlet switch 113 is configured for switching between connecting either the blood inlet 112 to the blood flow channel inlet 13 or the thrombolytic agent inlet 111 to the blood flow channel inlet 13. The inlet switches 13 may alternatively close both connections so that the blood flow channel 12 of the dialysis system 10 is disconnected from the blood inlet 112 as well as the thrombolytic agent inlet 111.

Under normal operation of the dialysis system 10, the blood inlet 112 is connected to the respective blood flow channel inlets 13 so that blood from the patient's blood stream may flow through the blood flow channels 12 of the plurality of filter sections 11 in the dialysis system 10. Each filter section 11 further comprises a dialysate flow channel 15 arranged alongside the blood flow channel 12 and a membrane 16 separating the blood flow channel 12 from the dialysate flow channel 15. Each membrane 16 is provided with a plurality of pores 17 through which substances are exchanged between a blood flow in the blood flow channel 12 and a dialysate flow in the dialysate flow channel 15. In this manner, toxins in the blood are allowed to pass through pores of the membrane and thereby the toxins are removed from the blood flow.

Over time, blood clots are formed in the blood flow channel 12, which may lead to clogging of the pores 17 of the membrane 16 and potentially also of the entire blood flow channel 12. Blood clotting decreases the efficiency of the dialysis through the membrane, jeopardizing the health of the patient. In order to prevent clogging or to remove blood clots from the blood flow channel 12, the maintenance device 100 provides means for maintenance of the blood flow channels 12.

The maintenance device 100 comprises a processing unit 130. The processing unit 130 is configured for determining whether a maintenance criterion is fulfilled for any of the blood flow channels 12 of the plurality of filter sections 11. Determining whether a maintenance criterion is fulfilled is determined for each of the filter sections individually and independently.

By way of example, a preventive maintenance criterion may be fulfilled if the time duration since a nearest preceding maintenance event for the filter section 11 is above a predetermined threshold. In this manner maintenance is performed on a regular, periodic basis even for blood flow channels 12 for which the filtering efficiency has not yet been impaired. By way of further example, a corrective maintenance criterion may be fulfilled if the presence of blood clots is detected in the flow channel.

Upon determining that a maintenance criterion is fulfilled for a blood flow channel 12, the processing unit 130 is configured for triggering a maintenance event for the filter section 11 for which the maintenance criterion is fulfilled. As part of the execution of the maintenance event, the processing unit 130 may send a control signal to the inlet switch 113 connected to a blood flow channel inlet 13 of the filter section 11 for which the maintenance criterion is fulfilled. As a response to receiving the control signal, the inlet switch may switch from connecting the blood flow channel inlet 13 to the blood inlet 112 and instead connecting the blood flow channel inlet 13 to the thrombolytic agent inlet. In this manner the blood flow through the blood flow channel 12 is stopped and instead the thrombolytic agent may be administered through the blood flow channel 12. The thrombolytic agent may thus flush the blood flow channel 12, dissolving blood clots present in the blood flow channel 12 with the purpose of restoring the blood flow channel 12 and the membrane 16 to a condition of full filtering capacity.

The maintenance device 100 illustrated in FIG. 1 further comprises a plurality of outlet switches 123, each of which is connected to a corresponding blood flow channel outlet 14 of a blood flow channel 12 in the plurality of filter sections 11. Each outlet switch 123 is further connected to a blood outlet 122 and a thrombolytic agent outlet 121. During normal operation of the dialysis system 10, the blood outlet 122 may return the cleaned blood flow from the blood flow channel 12 to the blood stream of the patient. During a maintenance event, if the thrombolytic agent being used is harmful to the human body, the thrombolytic agent outlet 121 may direct waste thrombolytic agent from the blood flow channel 12 to a waste reservoir configured to receive and store waste thrombolytic agent. Alternatively, if the thrombolytic agent being used is not harmful to the human body, the thrombolytic agent outlet 121 may direct waste thrombolytic agent to the bladder of the patient.

During the execution of a maintenance event, the processing unit 130 may send a control signal to the outlet switch 123 connected to the blood flow channel outlet of the filter section 11. As a response to receiving the control signal, the outlet switch 123 may switch from connecting the blood flow channel outlet 14 to the blood outlet 122 to instead connecting the blood flow channel outlet 14 to the thrombolytic agent outlet 121.

At the end of a maintenance event, the processing unit 130 may switch back to connecting the blood flow channel 12 of the dialysis system 10 to the blood inlet 112 and blood outlet 122 of the maintenance device 100, so that the filter section 11 is returned to filtering blood of the patient.

By way of example, a computer program product comprising computer-readable instructions may be loaded into the processing unit 130 such that when executed by a processing unit 130, the computer program product will cause the processing unit to perform the method described for automatic maintenance of the dialysis system 10. The computer program product may be provided on a tangible computer-readable medium provided with the computer-readable instructions, such as any computer-readable medium on which the computer-readable instructions may be stored.

As illustrated in FIG. 1, the maintenance device 100 comprises an inlet sensor 140 arranged at the conduit connecting each of the inlet switches 113 to the corresponding blood flow channel inlet 13. Further, the maintenance device 100 comprises an outlet sensor 141 arranged at the conduit connecting each of the blood flow channel outlets 14 with the corresponding outlet switches 123. The present inlet sensor 140 and outlet sensor 141 are configured to measure blood flow pressure before and after each individual blood flow channel 12. However, it is conceivable that the sensors may alternatively be sensors for blood flow rate, blood flow chemistry, blood flow ion content, electrical conductivity, ultrasonic transmission or reflection, or presence of blood clots. Changes in e.g. difference in blood flow pressure, or of any of the other specified parameters, before and after the blood flow channels 12 may be an indication of blood clotting or clogging in the blood flow channel 12. Thus, the present arrangement may enable identification of the onset of clogging of individual membranes 16 and or blood flow channels 12. The inlet sensor 140 and outlet sensor 141 measurements may be sent to the processing unit 130 for processing and thereby determining if a maintenance criterion based on sensor data is fulfilled.

In alternative variants of the maintenance device 100, an inlet sensor 140 may be arranged at the blood inlet 112, and an outlet sensor 141 may be arranged at the blood outlet 122. By the alternative arrangement, incoming arterial blood pressure and flow rate may be measured.

Upon finalizing the maintenance event for the filter section 11, the processing unit 130 may further be configured to determine whether the maintenance event was successful. By way of example, determination of whether the maintenance event was successful may be achieved by using the sensors 140, 141 again, to determine if the presence of blood clots can still be detected.

If the processing unit 130 determined that the corrective maintenance event was not successful, the processing unit may be configured to repeat the maintenance event, followed by another determination of whether the maintenance event was successful. The processing unit 130 may be configured to repeat the maintenance event up to a maximum number of attempts. If, after the last attempt, the processing unit 130 determines that the last maintenance event was successful, the maintenance device is returned to normal operation by the processing unit 130 sending signals to the inlet and outlet switches 113, 123 to close the thrombolytic agent inlet and outlet 111, 121, and open the blood inlet and outlet 112, 122. If, after the last attempt, the processing unit 130 determines that the last maintenance event was not successful, the processing unit 130 may classify the filter section 11 as irreparable. Upon the filter section 11 being classified as irreparable, the processing unit may be configured to send control signals to the inlet and outlet switches 113, 123 connected to a spare filter section 19 instead of the switches 113, 123 connected to the deemed irreparable filter section 11. As a response to the control signals the switches 113, 123 may connect the spare filter section 19 to the blood flow as a replacement for the deemed irreparable filter section 11. By the present arrangement, the number of filter sections 11,19 operating with blood flow may be kept constant, thereby maintaining full capacity of the dialysis system 10.

The maintenance device may further comprise an antenna 180 for wirelessly sending messages to external units. The message may include information about a status of the plurality of filter sections of the dialysis system. More specifically, the message may include information regarding a filter section being classified as irreparable and/or a spare filter section being connected to the blood flow and/or the number of remaining spare filter sections available in the system. The information may be sent to a device of the patient, such as a mobile phone, tablet, or computer. In this manner, the patient may be informed about whether there is a need to visit a hospital for a check-up or whether the dialysis system requires the attention of medical personnel. Alternatively, or additionally, the information may be sent to the hospital or the treating doctor. By way of example, the message may be sent via a router in the home of the patient forwarding it to the hospital via the internet.

It serves to mention that the dialysis system 10, and thus also the maintenance device 100 in connection with the dialysis system 10, may be implemented in different variants that may be arranged in relation to the patient in a number of different manners. By way of example, the dialysis system 10 may be implantable into a patient or it may be externally wearable by a patient such that the filter sections 11, and also the maintenance device 100, is external to the body of the patient. These systems may be carried by the patient for continuous cleaning of the blood from toxins. It is however conceivable that the dialysis system 10 may also be a stationary dialysis system 10 such as a stationary dialysis system 10 at a hospital.

Figure 2:
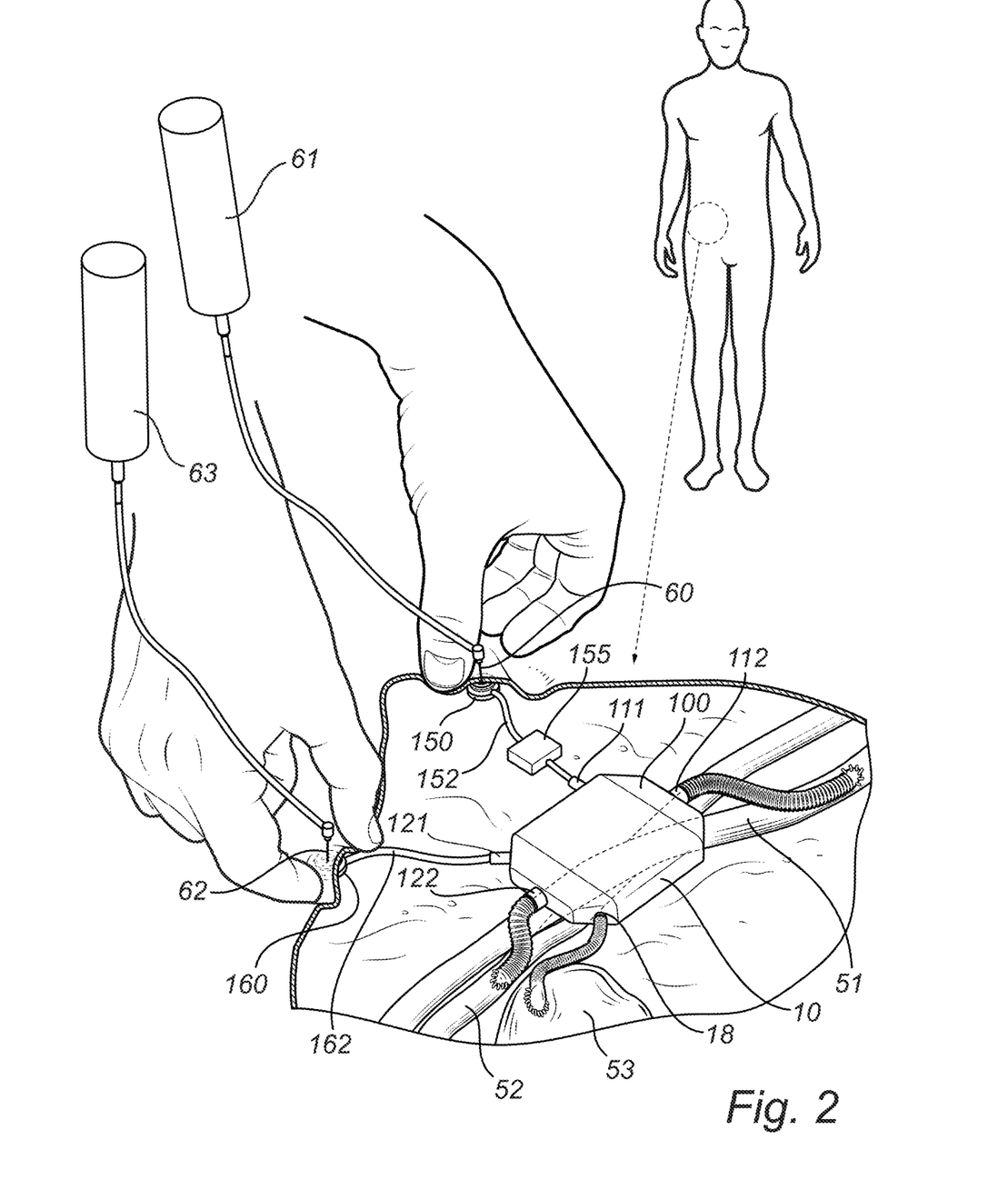
FIG. 2 illustrates an implantable dialysis system with a maintenance device, implanted into a patient, according to an example embodiment.

FIG. 2 illustrates an implantable dialysis system 10 with a maintenance device 100, implanted into a patient. As with conventional dialysis systems 10 without any maintenance device 100, blood flow from an artery 51 of the patient is directed to the dialysis system 10. In the present arrangement the blood flow from the artery 51 is received at the blood inlet 112 of the maintenance device 100 and from the maintenance device 100 the blood flow is distributed out to the different filter sections of the dialysis system 10, as described in relation to FIG. 1. The clean blood flows leave the dialysis system 10 via the blood flow channel outlets through the outlet switches and are recombined to a common clean blood flow being returned to the body of the patient via the blood outlet 122 into a vein 52 of the patient.

Depending on the type of dialysis system 10, waste dialysate may be discarded from the dialysis system 10 via a dialysate outlet 18 and transported to the bladder 53 of the patient, providing that the dialysate is not harmful to the human body.

In the present embodiment, a supply reservoir 150 has been arranged under the skin of the patient and connected to the thrombolytic agent inlet 111 of the maintenance device 100 via an inlet tube 152. The supply reservoir 150 is configured to store the thrombolytic agent, in order to supply a thrombolytic agent feed to the maintenance device 100 as a part of the execution of a maintenance event for maintenance of the dialysis system 10.

A dosage pump 155 is arranged at the thrombolytic agent inlet 111 side of the inlet tube 152. The dosage pump 155 is configured to pump the thrombolytic agent from the supply reservoir 150 to the blood flow channel via the maintenance device 100. The dosage pump 155 may be configured to provide the correct dosage of thrombolytic agent. Further, the dosage pump 155 may be communicatively connected to the processing unit 130 of the maintenance device 100, such that the processing unit may control the operation of the dosage pump 155, thereby providing the correct dosage of thrombolytic agent.

In the illustration of FIG. 2 the dosage pump is external to the maintenance device and serves all blood flow channels in the dialysis system 10. However, it is also conceivable that a plurality of dosage pumps may be arranged as a part of the maintenance device 100, so that each of the dosage pumps of the plurality of dosage pumps may serve individual blood flow channels.

A number of doses of thrombolytic agent can be stored in the supply reservoir 150, so that a number of maintenance events may be executed. However, if there were need for refilling the supply reservoir 150 with more thrombolytic agent, the supply reservoir may be accessible via a transdermal needle 60 that may be inserted through the skin of the patient to reach the supply reservoir 150. From a syringe 61 connected to the transdermal needle 60, the supply reservoir 150 may be refilled by additional thrombolytic agent.

In the present embodiment, a waste reservoir 160 has been arranged under the skin of the patient and connected to the thrombolytic agent outlet 121 of the maintenance device 100 via an outlet tube 162. The waste reservoir 160 is configured to store the waste thrombolytic agent discarded by the maintenance device 100 as part of executing a maintenance event for maintenance of the dialysis system 10.

By way of example, a pump may be arranged at the thrombolytic outlet 121, configured to pump waste thrombolytic agent from the dialysis system 10 to the waste reservoir 160. By way of further example, waste thrombolytic agent may alternatively be pumped from the dialysis system 10 to the waste reservoir by means of the dosage pump or by means of a pump arranged internally in the maintenance device 100.

The waste reservoir 160 may store waste thrombolytic agent from a number of maintenance events. However, if there were need for draining the waste reservoir 160 of waste thrombolytic agent, the waste reservoir may be accessible via a transdermal needle 62 that may be inserted through the skin of the patient to reach the supply reservoir 160. From a syringe 63 connected to the transdermal needle 62, the waste reservoir 160 may be drained by suction of the waste thrombolytic agent.

The maintenance device 100 may be available as a component in a kit of parts, comprising different components depending on requirements in different treatment cases. By way of example, a kit of parts for automatic maintenance of a dialysis system 10, may comprise a maintenance device 100, a supply reservoir 150 including the inlet tube 152, and a dosage pump 155. By way of further example, a kit of parts may, in addition to the listed parts, further comprise a waste reservoir 160 including the outlet tube 162. These two examples may be configured as add-ons to an already existing dialysis system 10.

Alternatively, kit of parts may include the parts listed above, and may further include also a dialysis system 10, such that the dialysis system 10 and the maintenance device 100 are connectable to each other, or pre-connected to each other.

Figure 3A:
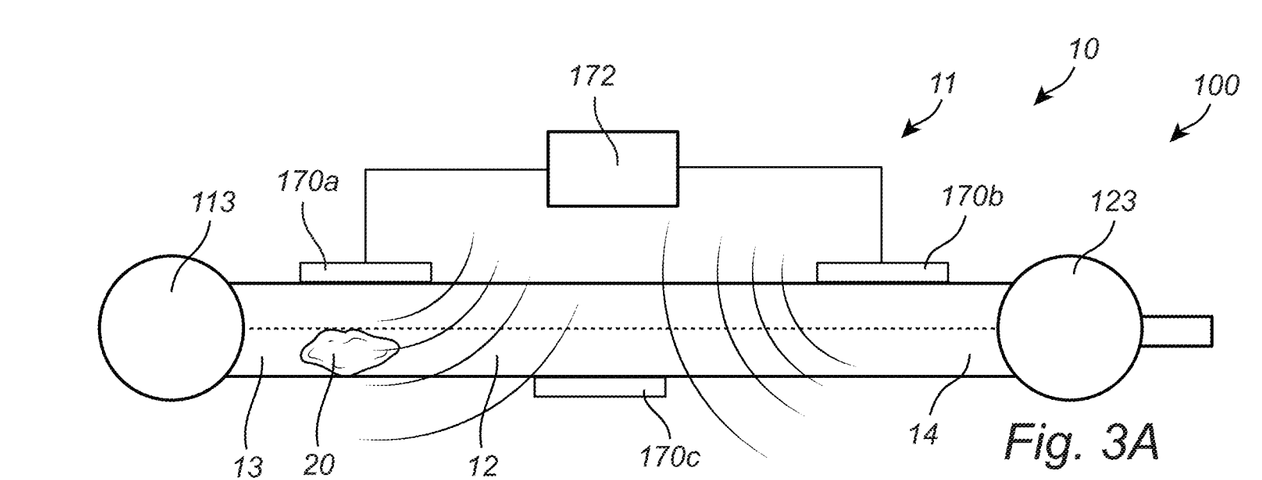
FIG. 3A and FIG. 3B illustrate how ultrasonic transducers may be arranged in a single filter section of the dialysis system, and the filter sections connection to the maintenance device, according to an example embodiment.
Figure 3B:
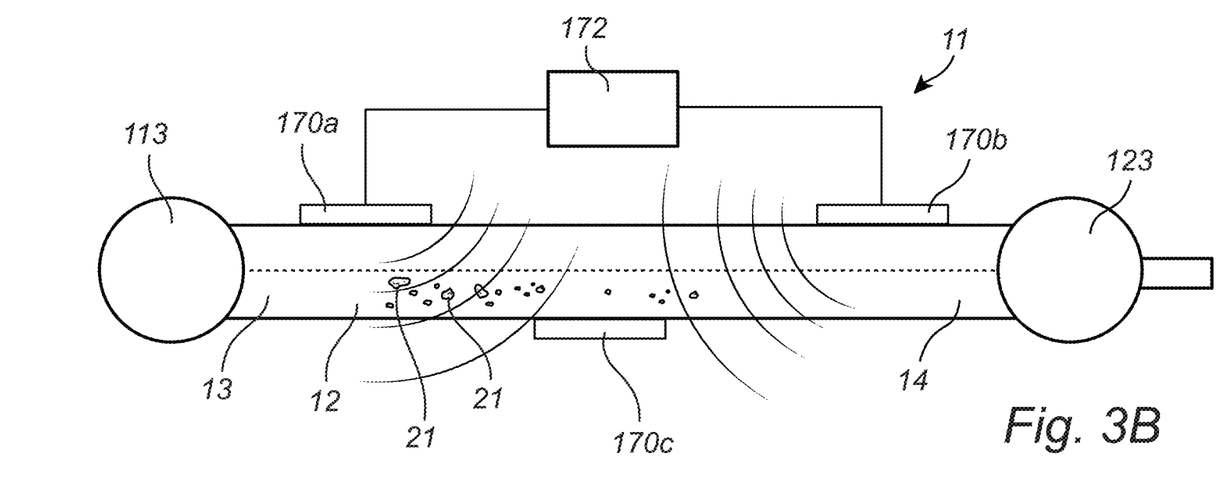

FIGS. 3A-B illustrate a single filter section 11 of the dialysis system 10, and connection of the filter section 11 to the maintenance device 100. The blood flow channel 12 is connected to the inlet switch 113 and the outlet switch 123 of the maintenance device. The maintenance device 100 may optionally comprise a number of, and in this case three, ultrasonic transducers 170a, 170b, 170c. Two of the ultrasonic transducers 170a, 170b are symmetrically arranged on one side of the blood flow channel 12, by the blood flow channel inlet 13 and the blood flow channel outlet 14, respectively. The third ultrasonic transducer 170c is arranged on the opposite side of the blood flow channel 12, in the center between the two other ultrasonic transducers 170a, 170b. The two ultrasonic transducers 170a, 170b are connected to a counter phase generator configured to provide a signal to each of the ultrasonic transducers 170a, 170b so that each of the ultrasonic transducers 170a, 170b emit an ultrasonic wave. The counter phase generator ensures that the signals for the two ultrasonic transducers 170a, 170b are kept in opposite phase, and consequently the emitted ultrasonic waves are also in opposite phase. The third ultrasonic transducer 170c is configured to detect any ultrasonic waves from the two other ultrasonic transducers 170a, 170b. If no blood clotting has occurred in the blood flow channel, the ultrasonic waves are not obstructed and may thus extinguish each other by destructive interference between the ultrasonic waves. The ultrasonic transducer 170c will hence not detect any ultrasonic wave.

However, if blood clotting has occurred, as illustrated in FIG. 3A by blood clot 20, the blood clot 20 may cause anisotropy in the blood flow channel 12 and the two ultrasonic waves may be obstructed by the blood clot 20 in the blood flow channel 12, and consequently full extinction of the ultrasonic waves will not occur. Upon interference between the two ultrasonic waves, there may thus be a remaining ultrasonic wave. The remaining ultrasonic wave resulting from anisotropy in the blood flow channel 12 may be detected by the third ultrasonic sensor 170c. In this manner, the blood flow channel 12 may be monitored for presence of blood clots 20. Even early wall deposits may be detected by the present arrangement, and by sending the detected signal to the processing unit of the maintenance device 100, the processing unit may trigger a maintenance event for the blood flow channel 12 already at an early stage when the maintenance event is likely of being successful.

Alternatively, or in addition to the detection of clotting, the arrangement of ultrasonic transducers 170a, 170b, 170c may also be used as a part of the maintenance event of the filter section 11. An ultrasonic transducer 170s, 170b, 170c may emit an ultrasonic wave into the blood flow channel 12 during the maintenance event. The ultrasonic wave may cause shaking or vibration in the blood flow channel 12 such that the declotting effect of the thrombolytic agent may be increased or amplified. This is illustrated by the blood clot 20 in FIG. 3A being dissolved into blood clot fragments 21 in FIG. 3B. By the present arrangement, it may be possible to use less thrombolytic agent in each maintenance event as compared to a maintenance event without any emitting of an ultrasonic wave.

By way of example, ultrasonic transducer 170a, 170b, 170c may be arranged on walls of the blood flow channel 12. Alternatively, ultrasonic transducer 170a, 170b, 170c may be arranged on the membrane 16.

The present arrangement may further be used for prevention of the onset of blood clotting.

Figure 4:
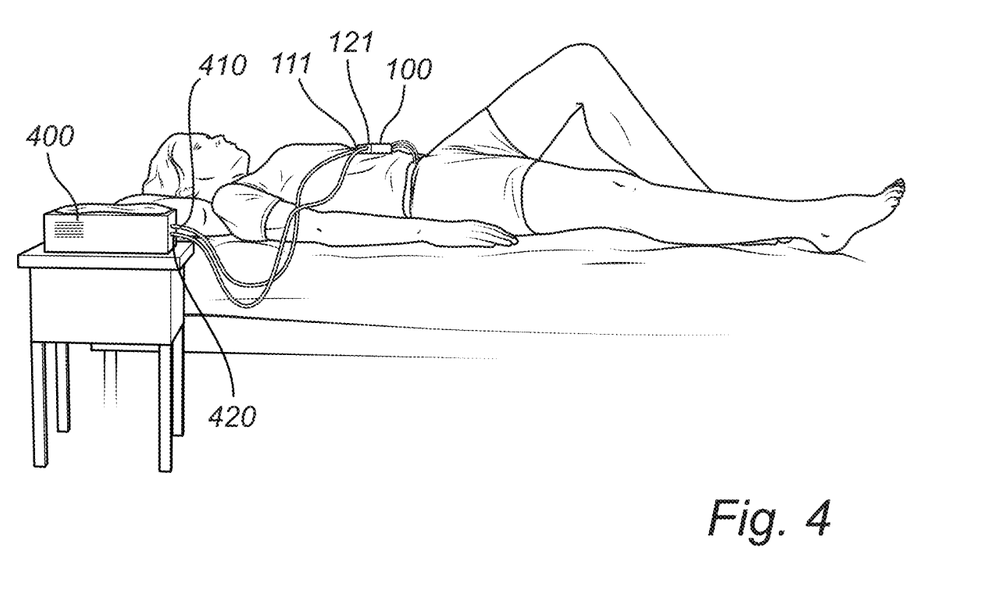
FIG. 4 illustrates the dialysis system with the maintenance device, being externally wearable by the patient, according to an example embodiment.

FIG. 4 illustrates the dialysis system 10 with the maintenance device 100, being externally wearable by the patient. In the present arrangement the patient always carries the system, just as with the case of an implantable system, and toxins are continuously filtered from the blood flow.

As opposed to having the maintenance device 100 connected to an implanted supply reservoir and/or an implanted waste reservoir, if the maintenance device 100 is externally worn, the maintenance device 100 may instead be connected to an external thrombolytic agent supply and waste apparatus 400. The thrombolytic agent inlet 111 of the maintenance device 100 may be connected to a thrombolytic agent supply outlet 410 of the external apparatus 400, whereby a thrombolytic agent feed is provided when required for maintenance. Further, the thrombolytic agent outlet 121 of the maintenance device 100 may be connected to a thrombolytic agent waste inlet 420, whereby waste thrombolytic agent may be discarded from the maintenance device and stored in the external apparatus 400.

Figure 5:
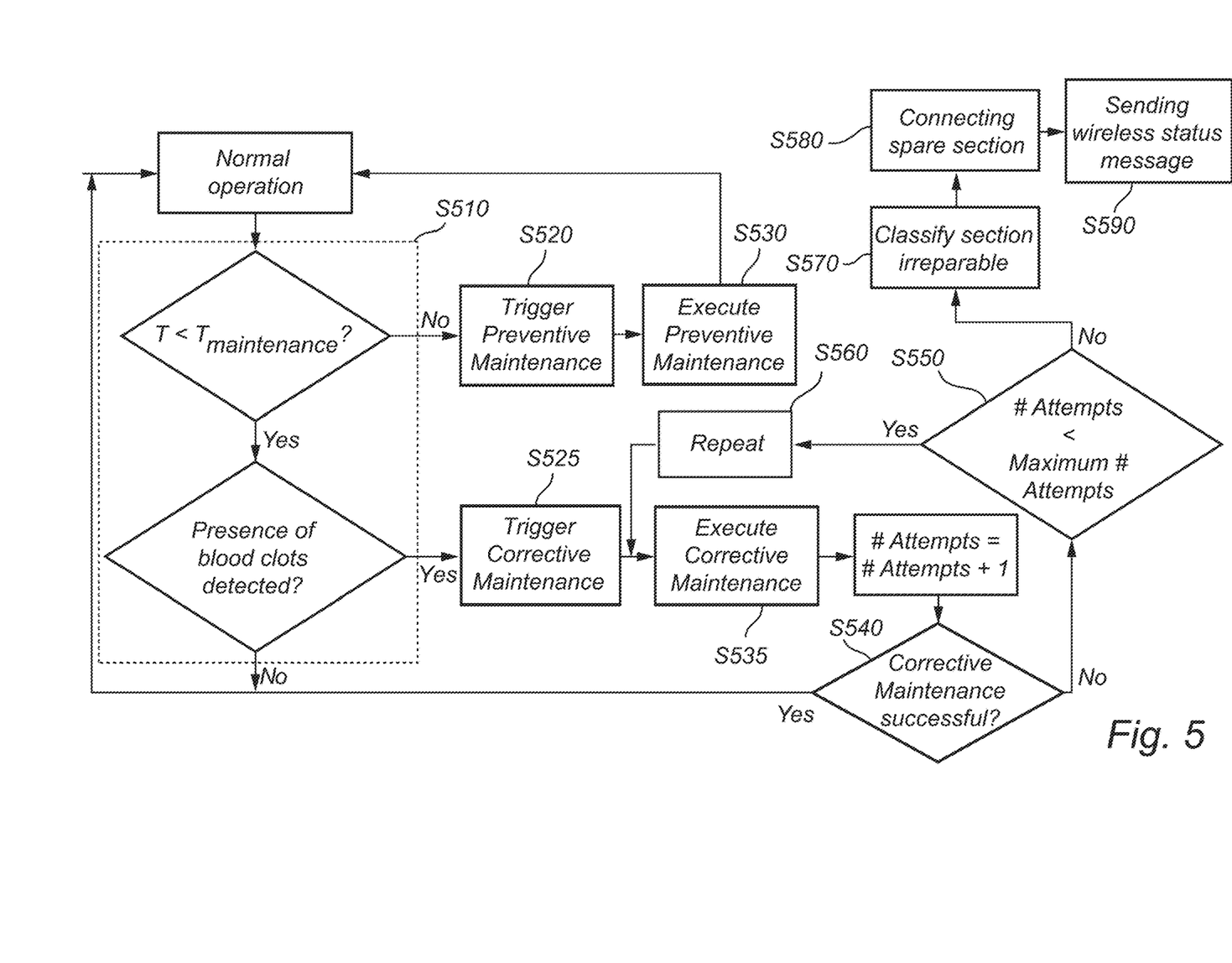
FIG. 5 illustrates a schematic block diagram shortly summarizing the method for automatic maintenance of a dialysis system, according to an example embodiment.

FIG. 5 illustrates a schematic block diagram shortly summarizing the method for automatic maintenance of a dialysis system 10. It should be understood that the steps of the method, although listed in a specific order herein, may be performed in any order suitable.

The method is intended for automatic maintenance of a dialysis system 10, wherein the dialysis system 10 comprises a plurality of filter sections 11, wherein each filter section 11 of the plurality of filter sections 11 comprises a blood flow channel 12, and a dialysate flow channel 15. The dialysis system 10 further comprises a membrane 16 separating the blood flow channel 12 from the dialysate flow channel 15 and having a plurality of pores 17 through which substances are exchanged between a blood flow in the blood flow channel 12 and a dialysate flow in the dialysate flow channel 15.

The method may comprise determining S510, for each filter section of the plurality of filter sections, whether a maintenance criterion is fulfilled. Determining whether a maintenance criterion is fulfilled may comprise determining whether a time duration since a nearest preceding maintenance event for the filter section is above a predetermined threshold. Determining whether a maintenance criterion is fulfilled may comprise measuring, by at least one sensor per filter section, a parameter of the blood flow flowing through the blood flow channel of the filter section, prior to entry into the blood flow channel, inside the blood flow channel, and/or after exiting the blood flow channel. The parameter may be any one from a blood flow rate, a blood flow pressure, a blood flow chemistry, a blood flow ion content, an electrical conductivity, an ultrasonic transmission or reflection parameter, and a presence of blood clots.

The method may comprise triggering S520 a periodic, preventive maintenance event for a filter section of the plurality of filter sections for which the maintenance criterion is fulfilled, based on whether the time duration since a nearest preceding maintenance event for the filter section is above a predetermined threshold.

The method may comprise triggering S525 a corrective maintenance event for a filter section of the plurality of filter sections for which the maintenance criterion is fulfilled, based on whether presence of blood clots or otherwise deterioration of performance of the filter section is detected by the at least one sensor per filter section.

The method may comprise executing S530 the periodic, preventive maintenance event for the filter section, following the triggering S520.

The method may comprise executing S535 the corrective maintenance event for the filter section, following the triggering S525.

The executing S530, S535 may comprise switching, at a blood flow channel inlet, from a blood inlet to a thrombolytic agent inlet. The executing S530, S535 may comprise switching, at a blood flow channel outlet, from a blood outlet to a thrombolytic agent outlet. The executing S530, S535 may comprise receiving, at the inlet of the blood flow channel, the thrombolytic agent from a supply reservoir configured to store the thrombolytic agent. The executing S530, S535 may comprise administering a thrombolytic agent to the blood flow channel of the filter section. The executing S530, S535 may comprise emitting, by one or more ultrasonic transducers, an ultrasonic signal into the blood flow channel, whereby the declotting effect of the applied thrombolytic agent is amplified. The executing S530, S535 may comprise discarding, at the outlet of the blood flow channel, the thrombolytic agent to a waste reservoir configured to store waste thrombolytic agent. The executing S530, S535 may comprise opening a blood flow channel inlet in a spare filter section, such that the number of filter sections operating with blood flow is constant, thereby maintaining full capacity of the dialysis system. The executing S530, S535 may comprise increasing an attempt variable by the value 1, upon finalizing a maintenance event. It should be noted that the executing S530 the preventive maintenance event and the executing S535 the corrective maintenance event may comprise the same selection of steps. However, the executing S530 the preventive maintenance event and the executing S535 the corrective maintenance event may alternatively comprise different selections of steps, from the above-mentioned options (e.g. using different types of thrombolytic agents, with or without ultrasound).

The method may comprise determining S540, upon finalizing the corrective maintenance event for the filter section, whether the maintenance event was successful.

If the determining S540 finds that the maintenance event was successful:

The system may be returned to normal operation by the blood flow channel being disconnected from the thrombolytic agent feed and reconnected to the blood flow feed.

If the determining S540 finds that the maintenance event was not successful:

The method may comprise determining S550 whether the maximum number of attempts of maintenance events has been reached.

If the determining S550 finds that the maximum number of attempts has not been reached:

The method may comprise repeating S560 the maintenance event up to a maximum number of attempts by returning to executing S535, and determining S540 whether the maintenance event was successful, after each repeated maintenance event.

If the determining S550 finds that the maximum number of attempts has been reached:

The method may comprise classifying S570 the filter section as irreparable.

The method may comprise connecting S580, upon the filter section being classified as irreparable, a spare filter section to the blood flow.

The method may comprise sending S590 a wireless message to an external unit, the wireless message including information about a status of the plurality of filter sections of the dialysis system.

The present disclosure has mainly been described with reference to a limited number of examples. However, as is readily appreciated by a person skilled in the art, other examples than the ones disclosed above are equally possible within the scope of the present disclosure, as defined by the appended claims.

What is claimed is:

1. A method for automatic maintenance of a dialysis system, wherein the dialysis system comprises a plurality of filter sections, wherein each filter section of the plurality of filter sections comprises a blood flow channel, a dialysate flow channel, and a membrane separating the blood flow channel from the dialysate flow channel and having a plurality of pores through which substances are exchanged between a blood flow in the blood flow channel and a dialysate flow in the dialysate flow channel, the method comprising:

determining, for each individual filter section of the plurality of filter sections, whether a maintenance criterion is fulfilled;

triggering a maintenance event for a filter section of the plurality of filter sections for which the maintenance criterion is fulfilled; and executing the maintenance event for the filter section, wherein said executing comprises:

administering a thrombolytic agent to the blood flow channel of the filter section.

2. The method according to claim 1, wherein the determining whether a maintenance criterion is fulfilled comprises:

determining whether a preventive maintenance criterion is fulfilled comprising determining whether a time duration since a nearest preceding maintenance event for the filter section is above a predetermined threshold.

3. The method according to claim 1, wherein the determining whether a maintenance criterion is fulfilled comprises:

determining whether a corrective maintenance criterion is fulfilled comprising measuring, by at least one sensor per filter section, at least one parameter of the blood flow flowing through the blood flow channel of the filter section, prior to entry into the blood flow channel, inside the blood flow channel, and/or after exiting the blood flow channel, wherein the at least one parameter being any one from a blood flow rate, a blood flow pressure, a blood flow chemistry, a blood flow ion content, an electrical conductivity, an ultrasonic transmission or reflection parameter, and a presence of blood clots.

4. The method according to claim 1, wherein the executing the maintenance event for the filter section further comprises:

switching, at a blood flow channel inlet, from a blood inlet to a thrombolytic agent inlet.

5. The method according to claim 4, further comprising:

opening a blood flow channel inlet in a spare filter section, such that the number of filter sections operating with blood flow is constant, thereby maintaining full capacity of the dialysis system.

6. The method according to claim 1, wherein the executing the maintenance event for the filter section further comprises:

receiving, at the inlet of the blood flow channel, the thrombolytic agent from a supply reservoir configured to store the thrombolytic agent.

7. The method according to claim 1, wherein the executing the maintenance event for the filter section further comprises:

discarding, at an outlet of the blood flow channel, the thrombolytic agent to a waste reservoir configured to store waste thrombolytic agent.

8. The method according to claim 1, wherein the method further comprises:

determining, upon finalizing the maintenance event for the filter section, whether the maintenance event was successful;

upon the maintenance event not being successful, repeating the maintenance event up to a maximum number of attempts;

determining, upon finalizing the maximum number attempts of maintenance events, whether the maintenance event was successful;

classifying, upon the maintenance event not being successful and after reaching the maximum number of attempts, the filter section as irreparable; and connecting, upon the filter section being classified as irreparable, a spare filter section to the blood flow.

9. The method according to claim 1, wherein the method further comprises:

sending a wireless message to an external unit, the wireless message including information about a status of the plurality of filter sections of the dialysis system.

10. The method according to claim 1, wherein the executing the maintenance event for the filter section further comprises:

emitting, by one or more ultrasonic transducers, an ultrasonic signal into the blood flow channel, whereby the declotting effect of the applied thrombolytic agent is amplified.

* * * * *